(12) United States Patent
Bronshtein

(10) Patent No.: US 9,469,835 B2
(45) Date of Patent: Oct. 18, 2016

(54) PRESERVATION BY VAPORIZATION

(76) Inventor: Victor Bronshtein, San Deigo, CA (US)

(*) Notice: Subject to any disclaimer, the term of this patent is extended or adjusted under 35 U.S.C. 154(b) by 1896 days.

(21) Appl. No.: 11/569,342

(22) PCT Filed: Jun. 1, 2005

(86) PCT No.: PCT/US2005/019285
§ 371 (c)(1),
(2), (4) Date: Nov. 17, 2006

(87) PCT Pub. No.: WO2005/117962
PCT Pub. Date: Dec. 15, 2005

(65) Prior Publication Data
US 2008/0229609 A1  Sep. 25, 2008

(51) Int. Cl.
*A01N 1/02* (2006.01)
*C12N 9/04* (2006.01)
*C12N 9/96* (2006.01)
*C12N 1/04* (2006.01)

(52) U.S. Cl.
CPC .............. *C12N 1/04* (2013.01); *A01N 1/0284* (2013.01); *C12N 9/0006* (2013.01); *C12N 9/96* (2013.01)

(58) Field of Classification Search
CPC .............. C12N 1/04; F26B 5/06; F26B 3/00; A23B 7/022; A23B 4/03; A01N 1/02
USPC .............................................................. 435/2
See application file for complete search history.

(56) References Cited

U.S. PATENT DOCUMENTS

| | | | | |
|---|---|---|---|---|
| 2,433,299 A | * | 12/1947 | Seegers | 435/188 |
| 3,261,694 A | * | 7/1966 | Forkner | 426/426 |
| 3,716,382 A | | 2/1973 | Chandrasekaran | |
| 4,520,574 A | | 6/1985 | Sugisawa et al. | |
| 5,298,261 A | | 3/1994 | Pebley et al. | |
| 5,514,586 A | * | 5/1996 | Hottinger et al. | 435/254.21 |
| 5,596,814 A | * | 1/1997 | Zingle et al. | 34/296 |
| 5,766,520 A | * | 6/1998 | Bronshtein | 264/4.6 |
| 6,509,146 B1 | | 1/2003 | Bronshtein | |
| 6,841,168 B1 | * | 1/2005 | Worrall | 424/484 |
| 2003/0219475 A1 | * | 11/2003 | Truong-Le | A61K 9/0019 424/450 |
| 2005/0074867 A1 | * | 4/2005 | Bronshtein et al. | 435/252.33 |

FOREIGN PATENT DOCUMENTS

| WO | WO/97/45009 | 12/1997 |
|---|---|---|
| WO | WO 99/27315 | * 6/1999 |

OTHER PUBLICATIONS

Heschel et al., 1999, WO1999027315, Partial Machine Translation from Patentscope, pp. 1-7.*

* cited by examiner

*Primary Examiner* — Sharmila G. Landau
*Assistant Examiner* — Sheridan Macauley
(74) *Attorney, Agent, or Firm* — Sheppard Mullin Richter & Hampton LLP

(57) ABSTRACT

Significant research is being done to develop and improve delivery mechanisms for biopharmaceuticals and vaccines, including pulmonary (inhalation), nasal, transdermal, and oral alternatives. Market projections indicate that the delivery of proteins and vaccines by inhalation and oral formulation has become and will continue to be increasingly important. These delivery mechanisms, to be effective, will require better stabilization of the biologicals so that they can maintain potency and effectiveness at ambient temperatures for extended periods of time. The novel Preservation by Vaporization (PBV) Technology described herein provides cost-effective and efficient industrial scale stabilization of proteins, viruses, bacteria, and other sensitive biologicals, thereby allowing a production of products that are not possible to be produced by existing methods. The suggested new PBV process comprises primary drying under vacuum from a partially frozen state (i.e. slush) at near subzero temperatures followed by stability drying at elevated temperatures (i.e., above 40 degrees Celsius). The new suggested method can be performed aseptically in unit doze format (in vials) and/or in bulk format (in trays, bags, or other containers). The drying can be performed as a continuous load process in a manifold vacuum dryer comprising a plurality (e.g., 30) of vacuum chambers attached to a condenser during the drying.

25 Claims, No Drawings

PRESERVATION BY VAPORIZATION

The present application is a National Phase Application of International Application PCT/US05/19285, filed Jun. 1, 2005, which claims benefit of U.S. Provisional Patent Application No. 60/576,394, filed Jun. 2, 2004.

FIELD OF THE INVENTION

This is an invention in the field of equipment and methods for stabilization (preservation) of biologically active molecules, viruses (vaccines), cells, and small multicellular specimens at ambient temperatures. The invention described herein can be used on a smaller scale as well as on an industrial scale. More particularly, the invention relates to methods and equipment for facilitating long-term storage and transportation of these labile biological materials at ambient temperatures in a dry, very viscous amorphous liquid or glass state.

This invention also relates to a technological process for integrating the following steps: preservation of the biological materials by vaporization in vials (unit dose format), or in a bulk format using trays, bags or other containers with or without subsequent milling and/or micronization of the preserved material. Milling and/or micronization allows to form dry powder, which can be used in mixed product (e.g., cereals) for different practical applications of vaccines and other biopharmaceuticals for both human and animal use, food (including baby food) and animal feed.

BACKGROUND OF THE INVENTION

The preservation and storage of biologically active materials, viruses, cells and small multicellular specimens is important for many applications, including research, food, microbiological, pharmaceutical and healthcare industries as well as for agriculture.

One of the most important criteria in evaluating the efficacy of practically all preservation techniques is how stable the resultant product is. It is well known that, in an aqueous phase, viral and bacterial vaccines, therapeutic proteins and other biologicals instantly lose activity during storage at ambient temperatures (AT). For example, according to Dr. Truong (as described in a U.S. patent application No. 20030219475), enveloped viruses—such as live influenza virus manufactured from egg allantoid fluid—loose one log of potency, defined as Tissue Culture Injectious Dose (TCID50), in less than two to three weeks when stored under refrigerated temperature, i.e. approximately 4 degrees Celsius. At room temperature conditions (approximately 25 degrees Celsius) and at warmer temperatures such as 37 degrees Celsius, the virus looses such potency in a matter of days to hours, respectively. An ability to store dehydrated biologically active materials at ambient temperatures for extended periods of time carries with it enormous benefits. Dehydrated reagents, materials, and biologicals are characterized by significantly reduced weight. In addition, they require less space for storage and, at the same time, offer increased stability.

Currently, measles vaccines are preserved by freeze-drying. Because the freeze-dried vaccines are stable only at near 0° C. temperatures, the measles vaccines need to be refrigerated at all times. World Health Organization (WHO) has estimated that just the maintenance of the existing "cold chain" in economically challenged countries (ECC) costs over $200 million annually. In addition, many rural areas do not have refrigeration at all, which makes it either practically impossible or very costly to administer existing measles vaccines in such areas.

Availability of stable at ambient temperature and more potent vaccines against MMR, tuberculosis, flu and other diseases will have an enormous impact on human health worldwide. Storage at ambient temperatures would eliminate the need for a cold chain, a costly and challenging logistical problem in many parts of the world, especially those parts where many of these vaccines are needed the most.

Existing methods for manufacture and storage of live vaccines require improvement for two major reasons. First, during manufacture, the vaccine is typically lyophilized or freeze-dried. Conventional freeze-drying is very damaging to cellular components and other biologicals, which, typically, results in reduced viability of the vaccine by a log or more. Second, conventionally freeze-dried products are stable only at or near 0° C., which requires that the vaccine be refrigerated from the time it is manufactured until the time it is administered. Hence, a so-called "cold chain" needs to be maintained during storage and transportation. In many instances, including transportation within the developing world and remote areas, refrigeration is either unavailable or problematic. Even if refrigeration is available, it significantly increases the costs of storage and transportation. Thus, development of a method for stabilizing vaccines so that they can be stored and transported at ambient temperatures is an important objective of this invention. So far, notwithstanding the attempts of numerous researchers, no such methods have been developed using freeze-drying, and the most common methods based on freeze-drying have failed to eliminate the need for the "cold chain."

Stabilization by Vitrification (Glass Formation)

While for a limited amount of time (several days), stabilization of sensitive biologicals, including biological macromolecules, viruses and cellular items, can be achieved in a liquid state, the long-term (several months, several years or more) stabilization of the biologicals requires arresting molecular mobility to stop degradation processes during storage. This can be achieved by vitrification, which is a transformation from a liquid into a highly immobile, non-crystalline, amorphous solid state, known as the "glass state."

A "glass state" is an amorphous solid state, which may be achieved by supercooling of a material that was initially in a liquid state. Diffusion in vitrified materials (i.e., glasses) occurs at extremely low rates (e.g., microns/year). Consequently, chemical and biological changes requiring the interaction of more than one moiety are practically completely inhibited. Glasses normally appear as homogeneous, transparent, brittle solids, which can be ground or milled into a powder. Above a temperature known as the glass transition temperature $T_g$, the viscosity drops rapidly and the material transforms from a glass state into what is known as a deformable "rubber state." As the temperature increases, the material transitions into a liquid state. The optimal benefits of vitrification for long-term storage may be secured only under conditions where $T_g$ is greater than the storage temperature.

Although scientists still dispute thermodynamic models that explain the transformation of highly supercooled liquids, or supersaturated solutions, into the "glass state" during cooling, vitrification has been broadly used to preserve biological and highly reactive chemicals. The basic premise of vitrification is that all diffusion limited physical processes and chemical reactions, including the processes responsible for the degradation of biological materials, stop in the glass state. This premise is based on Einstein's theory that establishes the relation between viscosity and diffusion. In general terms, glasses are thermodynamically unstable, amorphous materials that are mechanically stable at their very high viscosity ($10^{12}$-$10^{14}$ Pa·s.). A typical liquid has a flow rate of 10 m/s compared to $10^{-14}$ M/s in the glass state.

For many years, it has been well-known that biologicals can be preserved at −196° C. $T_g$ for pure water is about −145° C. If ice crystals form during cooling, the solution that remains unfrozen in the channels between ice crystals will vitrify at $T_g'$, which is higher than $T_g$ for pure water Biologicals that are rejected in the channels during ice growth will be stable at temperatures below $T_g'$.

The damaging effect of cryopreservation is mostly associated with freeze-induced dehydration, change in pH, increase in extracellular concentration of electrolytes, phase transformation in biological membranes and macromolecules at low temperatures, and other processes associated with ice crystallization. Potential cryodamage is a drawback in the methods that rely on freezing of biologicals. This damage could be decreased by using cryoprotective excipients (protectants), e.g., glycerol, ethylene glycol, dimethyl sulfoxide (DMSO), sucrose and other sugars, amino acids, synthetic, and/or biological polymers, etc.

Biologicals can be stabilized at temperatures substantially higher than −145° C. if they are placed in concentrated preservation solutions with high $T_g$. For example, for a solution that contains 80% sucrose, $T_g$ is about −40° C. A solution that contains 99% sucrose is characterized by $T_g$ of about 52° C. The presence of water in a sample results in a strong plasticizing effect, which decreases $T_g$. The $T_g$ is directly dependent on the amount of water present, and may, therefore, be modified by controlling the level of hydration—the less water, the higher the $T_g$. Therefore, the specimens (to be vitrified at an ambient temperature) must be strongly dehydrated by drying. However, drying can be damaging to biologicals. Therefore, to stabilize biologicals at a room temperature and still preserve their viability and functions, they need to be dried in the presence of a protective excipient (i.e., protectant) or a combination of excipients, which have a glass transition temperature $T_g$ higher than the room temperature.

There are at least two aspects of stabilization in a dry state that should be optimized to arrive at a method for preserving biologicals that results in a preserved material suitable for a long-term storage at ambient temperatures: (1) it is important to formulate an effective preservation solution that will not crystallize during the drying process and, at the same time, will reliably protect the biological from damage that may be caused by dehydration stress; and (2) the dehydration method must allow for an efficient and scalable way to dry the subject material.

Prior art teaches several methods for providing enhanced-stability preparations of labile biological materials in dehydrated form: freeze-drying, vacuum or air-drying by evaporation (preservation by evaporation), and preservation by foam formation.

Preservation by Evaporation

The application of drying for preservation of biopharmaceuticals was recorded several centuries ago. It was reported then that the sloe berries juice "may be reduced by gentle boiling to a solid consistence, in which state it will keep the year round." At the beginning of the last century, many scientists performed comparisons between the stabilizing effects of evaporation from the liquid state vs. freeze-drying. As a result, it has been established that activity of biologicals dried by evaporative drying of small drops is comparable to and in many cases even better than activity of freeze-dried samples. For example, it has been shown that labile enzymes (luciferase and isocitric dehydrogenase) can be preserved by evaporative drying for more than a year at 50° C. without any detectable loss of activity during drying and subsequent storage at 50° C. (Bronshtein, V., Frank, J. L., and Leopold, A. C. (1996). Protection of Desiccated Enzymes by Sugars. In: "Cryo 96 program", Abstract 22 of a Paper Presented at the 33rd Annual Meeting of the Society for Cryobiology, Indianapolis, Ind.; Bronshtein, V., and Leopold, A. C. (1996) Accelerated aging of dried luciferase and isocitrate dehydrogenase. Effect of sugar/enzyme mass ratio. In: "Cryo 96 program", Abstract 23 of a Paper Presented at the 33rd Annual Meeting of the Society for Cryobiology, Indianapolis, Ind.) Unfortunately, because dehydrated solutions containing protectors become very viscous, it takes long periods of time to evaporate water even from small drops of a solution. Therefore, until now, industrial applications have utilized freeze-drying methods because evaporative drying is a diffusion-limited process that is not scalable to industrial quantities.

Freeze-Drying (FD)

Freeze-drying, or lyophilization, has been known and applied to preserve various types of proteins, viruses, and cells, including RBCs, platelets, and microorganisms. FD consists of two major steps: primary drying and secondary drying.

Freeze-drying can be used to produce stable biologicals in industrial quantities. However, as a practical matter, it is very difficult (if not impossible) to develop a continuous load freeze-drying process for cost-effectively making industrial quantities of stable biologicals. In addition, it is very difficult to execute freeze-drying as a barrier process (i.e., a process where the operator is sufficiently separated from the material being preserved) in both vial for unit dose production and in bags, trays or other containers for bulk production. New methods are necessary to satisfy all requirements of industrial production.

Primary Freeze-Drying

The limitations of freeze-drying, as described above, result in part from a need to utilize low pressure (or high vacuum) during a freeze-drying process. A high vacuum is required because the temperature of the material during the primary freeze-drying should be below its collapse temperature, which is approximately equal to $T_g'$. At such low temperatures, the primary drying takes many hours (sometimes days) because the equilibrium pressure above ice at temperatures below −25° C. is less than 0.476 Torrs. Therefore, a new process must allow for shorter production times.

The low vacuum pressure used in the existing freeze-drying methods limits the amount of water that can be removed from a drying chamber to a condenser per one unit of time. Therefore, it is impossible to build an industrial manifold freeze-dryer with a volume of material to be dried in each chamber equal to several liters or more, which is necessary for an industrial scale production. New methods are necessary to allow for efficient industrial scale production of sufficiently large amounts of preserved biologicals.

In addition, such low water vapor pressures limit the selection of films that can be used to isolate the target material in bags from the environment of the chamber during the freeze-drying process. Currently the industry uses Lyoguard trays covered with Gore membranes. Gore membranes are made with pores to be permeable to water vapor, which is necessary for any drying process. Because of the presence of pores, Gore membranes are also permeable by some viruses.

Primary freeze-drying is performed by sublimation of ice from a frozen specimen at temperatures close to or below $T_g'$ that is a temperature at which a solution that remains not frozen between ice crystals becomes solid (vitrifies) during cooling. According to conventional beliefs, performing freeze-drying at such low temperatures is important for at least two reasons.

The first reason for which freeze-drying at low temperatures (i.e., below $T_g'$) is important is to ensure that the cake remaining after ice removal by sublimation (primary drying) is "solid" and mechanically stable, i.e., that it does not collapse. That is a valid reason. Keeping the cake in a mechanically stable "solid" state after primary freeze-drying is important to ensure effective reconstitution of the freeze-dried material. Several methods were proposed to measure the $T_g'$ for a specific material. These methods rely on different interpretations of the features that can be seen in DSC (Differential Scanning calorimeter) thermograms. The most reliable way to determine $T_g'$ is based on an evaluation of the temperature at which ice begins to melt and the concentration of water remaining unfrozen ($W_g'$) during slow cooling. The following relevant data have been reported:

Sucrose: $-38.8°$ C.$<Tg'<-37.55°$ C., and 18.76 wt %$<Wg'=1-Cg')<19.42$ wt %;

Glucose: $-59.9°$ C.$<Tg'<-49.37°$ C. and 18.76 wt %$<Wg'=1-Cg')<19.42$ wt %;

Sorbitol: $-54.44°$ C.$<Tg'<-52.03°$ C., and 18.76 wt %$<Wg'=1-Cg')<19.42$ wt %.

For a solution of bovine serum albumin in water $T_g'$ is $-20°$ C. and $W_g'$ is 20 wt %. For this reason, the primary freeze-drying should be performed at temperatures below $-20°$ C. in a temperature range called Intermediately Low Temperatures (ILT), which is approximately between $-25°$ C. and $-50°$ C.

The second reason typically advanced to support the importance of freeze-drying at low temperatures (i.e., below $T_g'$) is that the survival rate of biologicals after freeze-drying is higher if the primary freeze-drying is performed at lower temperatures. Two principal arguments are typically used to support this notion. The first one is that drying at lower temperatures is beneficial because it " . . . slows the kinetics of degradation reactions" (see for example, U.S. patent application Ser. No. 10/412,630). The second argument used to support the connection between freeze-drying at low temperatures and the survival rate of biologicals is that freeze-drying induced damage occurs primarily during the secondary drying after ice lyophilization is completed. (Webb, S. D. Effect of annealing lyophilized and spray-lyophilized formulations of recombinant human interferon-gamma. J Pharm Sci, 2003, 92 (4):715-729).

However, both of the above arguments are erroneous because the decrease in reaction rates expected from the Arrhenius kinetics is applicable only to unfrozen solutions. The reaction rates actually increase in frozen solutions because ice crystals concentrate solutes and biologicals in the channels remaining unfrozen between the crystals. In theory and in practice, freeze-drying ("FD") is very damaging for sensitive biologicals. Strong FD-induced injury occurs during both freezing (formation of ice crystals) and the subsequent equilibration of the frozen specimens at intermediately low temperatures during ice sublimation.

Well-known factors that cause cell damage during freezing include: freeze-induced dehydration, mechanical damage of cells during ice crystallization and recrystallization, phase transformation in cell membranes, increasing electrolyte concentration and others. However, possibly the principal factor that damages frozen biologicals is the occurrence of a large pH change in the liquid phase that remains unfrozen between ice crystals. This abnormal pH change, which can be as large as 5 units (i.e., pH>12), is associated with crystallization hydrolysis, as described in "Freezing Potentials Arising on Solidification of Dilute Aqueous Solution of Electrolytes." V. L. Bronshteyn, A. A. Chernov, J. Crystal Growth 112: 129-145 (1991).

Crystallization hydrolysis occurs because ice crystals capture positive and negative ions differently. This creates a significant (about $10^7$ V/m) electrical field inside ice crystals. Neutralization of this electrical field occurs due to electrolysis inside the ice crystals at a rate proportional to the constant of water molecule dissociation in ice. This neutralization results in a change of the pH of the liquid that remains between the ice crystals. The damaging effect of crystallization hydrolysis can be decreased by reducing the surface of ice that forms during freezing and by increasing the volume of the liquid phase that remains between the ice crystals. This remaining liquid also reduces the damaging effect of (i) the increasing electrolyte (or any other highly reactive molecules) concentration and (ii) the mechanical damage to cells between the ice crystals. The increase of the liquid between the ice crystals can be achieved by (i) increasing the initial concentration of of protectants added before freezing, and (ii) by decreasing the amount of ice formed in the sample.

Avoiding freezing to temperatures equal to $T_g'$ or below (at which freeze-drying is typically performed) will allow to significantly reduce the amount of damage in the preserved biological. Therefore, a new method that allows a preservation of biologicals without subjecting the biologicals to temperatures near or below $T_g'$ will significantly improve the quality of the preserved material.

Secondary Freeze-Drying

After the removal of ice by sublimation (primary drying) is complete, the sample may be described as a porous cake. Concentration of water in the sample at the end of primary drying is above the concentration of water $W_g'$ that remains unfrozen in the glassy channels between ice crystals at a temperature below $T_g'$. The data presented above show that $T_g'$ strongly depends on the composition of the solution, while for the majority of solutes $W_g'$ is about 20 wt %. At such high water concentrations, the glass transition temperature of the cake material is below the primary freeze-drying temperature, and/or significantly below $-20°$ C. Secondary drying is performed to remove the remaining (about 20 wt %) water and increase the glass transition temperature in the cake material. As a practical matter, secondary drying cannot be performed at $T_g'$ or lower temperatures because diffusion of water from a material in a glass state is extremely slow. For this reason, secondary drying is performed by heating the cake to a drying temperature $T_d$ that is higher than the glass transition temperature $T_g$ of the cake material at a given moment. If during the secondary drying step, $T_d$ is substantially higher than $T_g$, the cake will "collapse" and form a very viscous syrup, thereby making standard reconstitution impossible. Therefore, the collapse of the cake is highly undesirable.

The collapse phenomenon, which is kinetic by nature, has been extensively discussed in the literature. The rate of the collapse increases as the viscosity of the cake material decreases. To avoid or bring the collapse process to a negligible scale, $T_d$ is kept close to $T_g$ during the secondary drying, thereby ensuring that the viscosity of the cake material is high and the rate of the collapse slow.

During secondary drying, removal of water occurs through evaporation from the internal and external surfaces of the cake and is limited mostly by the rate of water diffusion inside the cake material. For this reason, secondary drying also takes many hours. Water diffusion inside the very viscous cake material during the secondary drying step is a very slow process that creates high gradients of water concentration inside the cake material. Therefore, at the end of the secondary drying step, $T_g$ of the cake material is normally still far below the maximum $T_d$ used during the secondary drying. In many cases, this explains why biologicals are not stable after preservation by freeze-drying.

To simplify the analysis, the characteristic time t of this process can be estimated using equation $t=h^2/D$, where h is a thickness of the specimen and D is the water diffusion coefficient. For water, D approximately equals $10^{-5}$ cm$^2$/sec. Given $D=10^{-5}$ cm$^2$/sec, it will take only about $10^{-3}$ sec to dry a small specimen with a thickness of 1 μm. However, D quickly decreases as the extent of dehydration, vitrification temperature ($T_g$), and, viscosity in the specimen increase. If $T_g$ can be increased during dehydration up to the temperature at which drying is performed, D will decrease (while viscosity will increase) approximately fourteen (14) orders of magnitude or more. As a result, the time required to remove water from a 1 μm specimen will be close to ten thousand (10,000) years. Therefore, as a practical matter, the glass state can only be achieved by cooling (at a constant pressure) and not by drying. For the same reason, when drying a biological solution, one cannot achieve a vitrification temperature $T_g$ higher than the temperature $T_d$ at which the drying is performed. This is a basic phenomenon that has been overlooked by many scientists who do not appreciate how slow the drying is at temperatures close to $T_g$ or below. For example, Roser et al. (U.S. Pat. No. 5,762,961), Schebor et al. (Journal of Food Engineering, 30, 269-282, 1996), Sun et al. (Physiologia Plantarum 90, 621-628, 1994), and many other researchers have reported values of $T_g$ much higher than the temperature at which the material was dried $T_d$. In these publications, to determine $T_g$, the authors must have misinterpreted their test results obtained by DSC (Differential Scanning calorimeter) devices. A more reliable measurement of $T_g$ should be performed by measuring the onset of thermally stimulated polarization (or depolarization) or the onset in specific heat change during a transition from the glass to liquid state.

Preservation by Foam Formation (PFF)

For more than fifty years, freeze-drying has been a dominant method for preservation of labile biologicals. This choice has been based on a conventional belief that freeze-drying is the only scalable (industrial) technology that can allow for a preservation of labile biologicals in a dry state. Other known methods, such as spray drying, drying with supercritical fluids, and other scalable methods of desiccation fail to preserve sensitive biologicals. During spray drying, small drops of biological or pharmaceutical suspensions or solutions are sprayed into a hot (above 100° C.) inert gas or air atmosphere, where they are quickly dried into a powder. The high temperatures used in this method cause unacceptable damage to sensitive biologicals. In addition, this method may not provide for sufficiently dehydrated biologicals and, depending upon a specific residual moisture requirements for product stability, additional drying by other means, such as vacuum shelf drying, may be required.

Approximately half a century ago, it was demonstrated by Annear that concentrated solutions and biological liquids that contained sugars or amino acids could be dried by foaming syrup under a vacuum. Annear applied this process to preserve several bacteria in a dry state. To obtain a syrup, Annear used sublimation and evaporation of water from the specimens. He did not believe that his process could be used for industrial applications. Later, in 1996, Roser and Gribbon (WO 96/040077) disclosed using exactly the same process to incorporate biologicals into a dry foam matrix. According to Roser and Gribbon, biological solutions should be evaporated first to obtain a "syrup" and, second, should be foamed by boiling the syrup under a vacuum. They actually defined the term "syrup" to mean a viscous solution that would foam during boiling. Thus, to foam specimens under vacuum, Annear had to obtain the syrup first by evaporation.

In 1996, a method was proposed for using the foaming process discovered by Annear to build a practical technology for preservation of sensitive biologicals in a dry state and a scalable preservation by foam formation protocol was developed (U.S. Pat. Nos. 5,766,520 and 6,306,345) These techniques, have been used to develop methods for stabilization at ambient temperatures for many bacteria, viruses, enzymes, therapeutic proteins and other molecular items. It also has been demonstrated that Annear's process can be scaled up to over 0.5-liter volumes by avoiding evaporation to obtain the syrup before the boiling begins. Since 1996, this innovative technology has been successfully applied to preserving sensitive biologicals.

After 1996, additional extensive studies have demonstrated the benefits of the PFF technology. (The PFF technology is also known as the VitriLife™ technology). Some of the results obtained after 1996 demonstrate that:

Molecular items like Amphotericin, Urokinas, Luciferase, β-Galactosidase, Ice Nucleating Protein, Taq DNA polymerase, and others can be stabilized at 37° C. or higher temperatures without any loss of activity.

Live viral vaccines from different taxonomic groups including, Herpesviridae (Bovine Rhinotracheitis), Paramyxoviridae (Measles, Bovine Respiratory Syndrome Virus (BRSV), Bovine Parainfluenza, Canine Parainfluenza, Canine Distemper), Flaviviridae (Bovine Viral Diarrhea), Parvoviridae (Canine Parvovirus), and retroviruses (MLV) can be stabilized at temperatures up to 37° C. without significant loss of activity.

Live bacterial vaccines like *Salmonella choleraesuis, Salmonella typhi, Bordetella bronchiseptica, Pasteurella multocida* and *Pasteurella haemolytica*, and many other bacteria including *E. coli* and *L. Acidophilus* can be effectively stabilized at 37° C. or higher temperatures.

At the same time, known attempts to preserve sensitive biologicals by conventional freeze-drying technology, in many cases, resulted in 10% or less survival yield and limited stability at ambient temperatures, i.e., without refrigeration. For example, survival yield of BRSV after conventional freeze-drying was less than 10% of a control sample. However, no detectable loss in the BRSV survival rate was observed in the specimens preserved by using preservation by foam formation. In 2002, the VitriLife™ technology was acquired to Avant Immunotherapeutics, Inc. (Avant).

The advantages of vitrification technology have not been fully utilized for achieving long-term stability of labile biological materials at ambient temperatures. Existing methods of ambient temperature preservation by drying are designed for laboratory scale processing of relatively small quantities of materials in unit dose vials, which makes these methods incompatible with large scale commercial operations. Technical problems related to monitoring of the glass transition temperature also have also presented obstacles to commercial implementation. While drying and vitrification technology are potentially attractive as scalable methods for long-term efficient storage of biological materials a number of problems need to be addressee before the advantages of storage in the glass state can be commercially exploited.

Despite the many benefits of the PFF (VitriLife™) technology, the technology also has some drawbacks. If one uses the approach described by Roser and Gribbon (WO 96/040077) and applies the evaporation to obtain a syrup, one will quickly find that in many cases or in a portion of vials, the boiling and foaming will not take place at all, even after an application of a high vacuum because the vapor phase cannot nucleate in a highly viscous syrup. This phenomenon makes practically impossible to validate an industrial scale PFF process developed in a lab for a specific biological. The process disclosed by Bronshtein in 1996 (U.S. Pat. No. 5,766,520) provides for a boiling step before the high viscosity of the material is achieved. The major drawbacks of that process are that it is characterized by uncontrollable eruptions of the material during boiling. These eruptions result in a portion of material splattered on the walls of the vials, which can pollute stoppers. In addition, some of such material may be released from the vials into the drying chamber. To soften the eruption during boiling and to make the boiling more gentle, it has been proposed to use two dimensional temperature/pressure application protocols that reduce overheating to an acceptable level. However, this protocol is difficult to implement and is difficult to reliably reproduce with different formulations. In many cases special processing requires to initiate nucleation of vapor bubbles (boiling) (U.S. Pat. No. 6,884, 866) of the syrup obtained by evaporation.

Therefore, the PFF process is characterized by a number of significant drawbacks that severely limit its application on an industrial scale. Consequently, a new process free of the drawbacks associated with the PFF methods is necessary to improve preservation of biologicals on an industrial scale.

SUMMARY OF THE INVENTION

The present invention includes new and advantageous methods and equipment for preserving bioactive materials for storage and transportation. Preservation by Vaporization (PBV) is a new method for preserving sensitive biologicals. The method comprise two major steps: primary drying and stability drying. The primary drying step is performed by intensive vaporization (sublimation, boiling and evaporation) of water at temperatures significantly (about 10° C. or more) higher than $T_g'$ from a partially frozen and at the same time overheated state (when a vacuum pressure is below the equilibrium pressure of water vapor) of a biological material. The material being preserved can take many various forms, including a biological solution, biological suspension and a biological (e.g, bacteria, viruses, therapeutic proteins encapsulated in hydrogels, etc.).

At the end of the primary drying step, the material being preserved is mechanically stable (e.g., it does not collapse) at a room temperature under high vacuum. Thereafter, stability drying is performed to increase the glass transition temperature of the dry material to make it mechanically stable at ambient temperatures without vacuum and to maximize the potency and viability of the biological after a long-term storage and/or transportation at ambient temperatures.

Preservation of hydrogels (including an alginate gel) by drying is more effective when the size of hydrogel particles is small (about 1 mm, or below). One reason that may explain that phenomenon is that the growth of vapor bubbles nucleated inside gel particles is limited by high viscosity inside the gel.

The containers (e.g., bags) for bulk drying pursuant to this invention allow to aseptically introduce a fluid (e.g., a biological solution or viral or cellular suspension) into a container, aseptically dry the fluid, aseptically store the dry specimen in the container, or aseptically transfer the dried material from the container to other devices for downstream processing (e.g., milling).

PBV process is beneficial as compared to the more conventional freeze-drying processes because inter alia: (i) it allows for a significantly faster preservation of biologicals, (ii) it can be efficiently performed at higher vacuum pressures (e.g., about 1 to 3 Torrs) and (iii) it produces preserved biologicals that can be stored and transported for extended periods of time without refrigeration.

The bags (or other containers) used for processing pursuant to the claimed inventive methods can have lower coefficient of permeation for water vapor than a conventional Gore membrane (expanded polytetrafluoroethylene) that contains 0.2 micron pores. For example, 10 to 50 micron (thickness) polypropylene or polyurethane breathable membranes from Mylan Technologies Inc., or Inspire wound dressing films from InteliCoat Technologies can be used to replace Gore membranes in the design of the containers (e.g., bags) used for drying. In addition, the containers that utilize polypropylene or polyurethane membranes are less expensive than the trays commonly used in the industry for such applications (i.e., Lyogard trays) covered with expensive membranes (e.g., Gore membranes).

The use of polypropylene or polyurethane membranes in the design of containers (e.g., bags) allows to make the drying a barrier aseptic process. At the same time, because such membranes are characterized by a limited mechanical strength, to address that issue, a "sandwiched" design that comprises a breathable membrane between two low-cost porous membranes (e g., Sartorius membranes for ultrafiltration) characterized by a higher permeability to water vapors and by a higher mechanical strength.

Dedicated, novel and specially designed equipment will allow to fully utilize the benefits of the new PBV method disclosed herein on an industrial scale. Such equipment can be designed as a manifold dryer as because the new PBV method does not require processing under a low vacuum pressure. One suggested design of an industrial manifold PBV dryer comprises drying chambers and a large-scale condenser. Drying chambers can be attached to the condenser by a plurality of connectors. The connectors contain vacuum valves that control the flow of air or water vapors from the drying chambers into the condenser. The material to be dried by the suggested new methods will be placed in a drying chamber. Appropriate heat will be provided by a heating source or sources to compensate for the loss of energy due to evaporation during the primary drying process. A heat exchanger can be used to cool the material to about −110° C. (thereby freezing it) before drying it. In some instances, to ensure that freezing takes place at temperatures not significantly below −10° C., special measures may need to be taken to nucleate ice crystals for example, ice nucleating bacteria can be use used for this purpose.

The proposed equipment may also have a control system (e.g., electrical or computer-based apparatus) to provide for proper process control of the various steps of the new method. For example, the heating step and the gas flows between the chambers and the condenser may be appropriately controlled. The control system can be designed and programmed to provide for automatically staggered drying processes in the chambers. Thus, each chamber will complete the drying at a different time, which in turn will allow for a continues load processing. The novel equipment design allows to connect a new chamber to the source of vacuum (e.g., a condenser) and disconnect a chamber from the source of vacuum when the drying process within that chamber is finished. Connecting and disconnecting chambers to the source of vacuum does not have to result in a physical detachment or moving of chambers. Chambers can be disconnected from the source of vacuum by a valve or another device. However, chambers that allow for physical detachments may provide additional benefits because it is considerably easier and less expensive to sterilize and maintain sterile the chambers as opposed to maintaining sterile the entire set of equipment.

The proposed new methods in conjunction with the proposed new equipment design allow for a manufacture on an industrial scale of preserved biologicals that can be stored and transported without refrigeration for extended periods of time. At the same time, the proposed new methods and equipment allow to conduct such manufacturing processes at the speeds and with the efficiency considerably greater than the speeds and efficiency available through any currently known methods.

DEFINITIONS

It is to be understood that this invention is not limited toga particular method, device or biological system, which can vary without departing from the spirit and scope of the present invention. The terminology and definitions used in this disclosure are for the purpose of describing particular embodiments only, and are not intended to be limiting. However the terminology defines the meaning of the words in the scope of this document. As used in this specification and the appended claims, the singular forms "a", "an" and "the" include plural referents unless the context in which they are used unambiguously dictates otherwise. Whether or not a defined term is capitalized in the text of this disclosure shall have no substantive effect upon its meaning.

The technical and scientific terms used herein should be in agreement with the terms commonly used by one of ordinary skill in the art to which the invention pertains. For this reason, unless expressly stated herein otherwise, the express definitions contained in U.S. Patent Application No. 2003/0219475 A1 (Vu Truong-Le, "Preservation of Bioactive Materials by Freeze Dried Foam.") will be used and incorporated herein by reference.

"Ambient Temperatures" are those at any given time in a given environment. Typically, ambient room temperature (RT) is about 22 degrees Celsius. Here, for the sake of clarity we may refer to a temperature approximately between −10 degrees Celsius and +40 degrees Celsius as an ambient temperature.

"Boiling" refers to the rapid phase transition from liquid to vapor that takes place when the temperature of a liquid is above its boiling temperature under specific conditions. The boiling temperature, as is well known to those skilled in the art, is the temperature at which the vapor pressure of a liquid is equal to the applied pressure. During the process of boiling, the vapor bubbles nucleate within liquid.

"Evaporation" means a process of movement of molecules through the liquid-gas interface from the surface of a liquid into a gas phase that already exists. Evaporation does not necessarily require overheating and nucleation of vapor bubbles.

"Sublimation" or "Freeze-Drying" means a process of movement of molecules from solid crystallized state directly into a gas phase through a crystal-gas phase interface.

"Vaporization" means a movement of molecules into a gas phase by Evaporation, Sublimation, or Boiling.

"Buffer" means a buffered solution that resists changes in pH by the action of its acid-base conjugate components. The pH of the buffer will generally be chosen to stabilize the active material of choice, and will be ascertainable by those skilled in the art. Generally, the pH of the buffer will be in the range of physiological pH, although some proteins, can be stable at a wider range of pHs, e.g., acidic pH. Thus, preferred pH ranges are from about 1 to about 10, with from about 3 to about 8 being particularly preferred. Even more preferably, pH is in the range from about 6.0 to about 8.0. Yet more preferably, pH is in the range from about 7.0 to about 7.4, and most preferably, pH is in the range between about 7.0 and about 7.2. Suitable buffers include a pH 7.2 phosphate buffer and a pH 7.0 citrate buffer. As will be appreciated by those skilled in the art, there is a large number of suitable buffers that may be used. Suitable buffers include, but are not limited to, potassium phosphate, sodium phosphate, sodium acetate, histidine, imidazole, sodium citrate, sodium succinate, ammonium bicarbonate and carbonate. Generally, buffers are used at molarities from about 1 mM to about 2 M, with from about 2 mM to about 1 M being preferred, and from about 10 mM to about 0.5 M being especially preferred, and 25 to 50 mM being particularly preferred.

"Dry" refers to a material with a residual moisture content less than about 10%. Dried compositions are commonly dried to residual moistures of 5% or less, or between about 3% and 0.1%.

"Protective Excipients" or "Protectants" (e.g., including, but not limited to cryoprotectants and lyoprotectants) generally refer to compounds or materials that are added to avoid injury of the therapeutic agent or a biological during a dry process and afterwards. Suitable excipients include, but are not limited to, proteins such as human and bovine serum albumin, gelatin, immunoglobulins, carbohydrates including monosaccharides (galactose, D-mannose, sorbose, etc.) and their not reducing derivatives (e.g methylglucoside), disaccharides (trehalose, sucrose, etc.), cyclodextrins, and polysaccharides (raffinose, maltodextrins, dextrans, etc.); an amino-acid such as monosodium glutamate, glycine, alanine, arginine or histidine, as well as hydrophobic amino acids (tryptophan, tyrosine, leucine, phenylalanine, etc.); a methylamine such as betaine; an excipient salt such as magnesium sulfate; a polyol such as trihydric or higher sugar alcohols, e.g. glycerin, erythritol, glycerol, arabitol, xylitol, sorbitol, and mannitol; propylene glycol; polyethylene glycol; Pluronics; surfactants; and combinations thereof.

"Co-solutes" can be present in the formulations and compositions of the invention in small concentration that are much smaller than the concentration of sugars and other Protestants. Co-solutes can be present in formulations of the invention in amounts of about 0.01 weight percent to about several weight percent. Similar to that reported by other people We have found that survival of some biologicals after drying could be improved if the hydrojel, solution, or suspension of the method can include co-solutes (surfactants and/or a zwitterions). Surfactants can include, e.g., polyethylene glycol sorbitan monolaurates (e.g., Tween 80), polyoxyethylenesorbitan monooleates (e.g., Tween 20), or block polymers of polyethylene and polypropylene glycol (e.g., Pluronic F68), and/or the like. Zwitterions of the method can include, e.g., arginine, histidine, glycine, and/or the like. We believe that it is well known that the co-solutes like polyethylene glycol, polypropylene glycol, polyethylene glycol/polypropylene glycol block copolymers, polyethylene glycol alkyl ethers, polypropylene glycol alkyl ethers, polyethylene glycol/polypropylene glycol ether block copolymers, alkylarylsulfonates, phenyl sulfonates, alkyl sulfates, alkyl sulfonates, alkyl ether sulfates, alkyl aryl ether sulfates, alkyl polyglycol ether phosphates, polyaryl phenyl ether phosphates, alkyl sulfosuccinates, olefin sulfonates, paraffin sulfonates, petroleum sulfonates, taurides, sarcosides, fatty acids, alkylnaphthalenesulfonic acids, naphthalenesulfonic acids, lignosulfonic acids, condensates of sulfonated naphthalenes with formaldehyde, or condensates of sulfonated naphthalenes with formaldehyde and phenol, lignin-sulfite waste liquor, alkyl phosphates, quaternary ammonium compounds, amine oxides, betaines, and/or the like. Tween® and Pleuronic® surfactants, such as, e.g., polyethylene glycol sorbitan monolaurate, polyoxyethylenesorbitan monooleate, or block copolymers of polyethylene and polypropylene glycol and many others could be included in the formulation prior to drying, however, the optimum concentrations of the co-solutes for different biologicals are different and should be determined experimentally.

"Glass," "Gassy State," or "Glassy Matrix," refers to a liquid that has lost its ability to flow, i.e. it is a liquid with a very high viscosity, wherein the viscosity ranges from $10^{10}$ to $10^{14}$ pascal-seconds. It can be viewed as a metastable amorphous system in which the molecules have vibrational motion but have very slow (almost immeasurable) rotational and translational components. As a metastable system, it is stable for long periods of time when stored well below the glass transition temperature.

"Glass Transition Temperature" is represented by the symbol $T_g$ and is the temperature at which a composition changes from a glassy or vitreous state to a syrup or rubbery state during warming. Generally, $T_g$ is determined using differential scanning calorimetry (DSC) and is typically taken as the temperature at which onset of the change of heat capacity (Cp) of the composition occurs upon scanning through the transition. The definition of $T_g$ is always arbitrary and there is no present international convention that applies. The $T_g$ can be defined as the onset, midpoint or endpoint of the transition. For the purposes of this invention and disclosure we will use the onset of the changes in Cp when using DSC. See the article entitled "Formation of Glasses from Liquids and Biopolymers" by C. A. Angell: Science, 267, 1924-1935 (Mar. 31, 1995) and the article entitled "Differential Scanning calorimetry Analysis of Glass Transitions" by Jan P. Wolanczyk: Cryo-Letters, 10, 73-76 (1989). For a detailed mathematical treatment, see "Nature of the Glass Transition and the Glassy State" by Gibbs and DiMarzio: Journal of Chemical Physics, 28, NO. 3, 373-383 (March, 1958).

"Pharmaceutically Acceptable" excipients (vehicles, additives) are those which can reasonably be administered to a subject mammal to provide an effective dose of the active ingredient employed. Preferably, these are excipients which the Federal Drug Administration (FDA) have to date designated as ' Generally Regarded as Safe' (GRAS). "Pharmaceutical composition" refers to preparations which are in such a form as to permit the biological activity of the active ingredients to be unequivocally effective, and which contain no additional components which are toxic to the subjects to which the composition would be administered.

"Polyol" means a substance with multiple hydroxyl groups, and includes, e.g., sugars (reducing and nonreducing sugars), sugar alcohols and sugar acids. Preferred polyols herein have a molecular weight which is less than about 600 kDa (e.g. in the range from about 120 to about 400 kDa). A "reducing sugar" is a polyol which contains a hemiacetal group that can reduce metal ions or react covalently with lysine and other amino groups in proteins. A "nonreducing sugar" is a sugar which does not have these properties of a reducing sugar. Most of monosaccharides are reducing sugars including fructose, mannose, maltose, lactose, arabinose, xylose, ribose, rhamnose, galactose and glucose. Nonreducing sugars include sucrose, trehalose, sorbose, melezitose and raffinose. Mannitol, xylitol, erythritol, threitol, sorbitol and glycerol are examples of sugar alcohols. Methylglucoside and 2-dioxyglucose are examples of not reducing derivatives of monosaccharides, As to sugar acids, these include L-gluconate and metallic salts thereof.

"Powder" means a composition that consists of finely dispersed solid particles that are relatively free flowing and capable of being readily dispersed in an inhalation device and subsequently inhaled by a patient so that the particles are suitable for intranasal or pulmonary administration via the upper respiratory tract including the nasal mucosa.

"Storage Temperature" for a composition is the temperature $(T_s)$ at which dry composition can be stored to maintain the stability of the product over the shelf life of the composition in order to ensure a consistently delivered dose. This temperature is initially determined by the manufacturer of the composition and approved by a governmental agency responsible for approval of the composition for marketing (e.g., the Food and Drug Administration in the U.S. for drug products). This temperature will vary for each approved drug or other product depending on the temperature sensitivity of the active drug and other materials in the product. The recommended storage temperature will vary from about 0 degrees C. to about 40 degrees C., but A biologically active material is said to "retain its biological activity" in a pharmaceutical or other composition, if the biological activity of the biologically active material, such as an enzyme, at a given time is within about 10% (within the errors of the assay) of the biological activity exhibited at the time the subject composition was prepared as determined in a binding assay. In the case of living viruses or bacteria, biological activity can be considered retained when the viral titer or colony count of the composition is within one log of the initial titer or count. For live cells, the biological activity is considered retained when the live cell count of the composition is within 50% of the initial count. One log FFU/ml is approximately equal to one log Tissue Culture Infectious Dose per ml (log TCID50/ml).

A biologically active material "retains its chemical stability" in a pharmaceutical or biological composition, if the chemical stability at a given time is such that the biologically active material is considered to retain its biological activity as defined herein. Chemical stability can be assessed by detecting and quantifying chemically altered forms of the biologically active material. Chemical alteration may involve size modification (e.g. clipping of proteins) which can be evaluated using size exclusion chromatography, SDS-PAGE and/or matrix-assisted laser desorption ionization/time-of-flight mass spectrometry (MALDI/TOF MS). Other types of chemical alteration include charge alteration (e.g., occurring as a result of deamidation) which can be evaluated by ion-exchange chromatography or other methods.

A biologically active material "retains its physical stability" in a pharmaceutical or biological composition if it shows no significant increases in aggregation, precipitation and/or collapse upon visual examination of color and/or clarity, or as measured by UV light scattering or by size exclusion chromatography.

A "Stable" formulation or composition is one in which the biologically active material therein essentially retains (depending upon a specific application) its physical stability and/or chemical stability and/or biological potency during storage and/or transportation. Various analytical techniques for measuring stability are known in the art and are reviewed, e.g., in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993). Stability can be measured at a selected temperature for a selected time period. Trend analysis can be used to estimate an expected shelf life before a material has actually been in storage for that time period. For live influenza viruses, stability is defined as the time it takes to loose 1 log of FFU/ml or 1 log of TCID50/ml. Preferably, the composition is stable at a room temperature for at least three months, or at 40 degrees Celsius for at least 1 month, and/or stable at about 2-8 degrees Celsius for at least 1 year. Furthermore, the composition is preferably stable following freezing (to, e.g., −70 degrees Celsius) and thawing of the composition.

A "therapeutically effective amount" of a biologically active material refers to an amount effective in the prevention or treatment of a disorder or a disease wherein a "disorder" is any condition that would benefit from treatment with the biologically active material. This includes chronic and acute disorders or diseases including those pathological conditions which predispose the mammal to the disorder in question.

"Treatment" refers to both therapeutic treatment and prophylactic or preventative measures. Those in need of treatment include those already with the disorder as well as those in which the disorder is to be prevented.

"Unit dosage" refers to a receptacle containing a therapeutically effective amount of a composition of the invention.

DETAILED DESCRIPTION OF THE INVENTION

The novel methods and equipment of the present invention allow for extended storage and transportation of bioactive materials at ambient temperatures.

It has been commonly known to avoid or minimize freezing of biologicals because freezing is considered by many to be a damaging process. However, freezing at near −0° C. temperatures may be not damaging (or at least is less damaging compared to freezing at or to −20° C. or below) because the pH change associated with crystallization hydrolysis is proportional to the surface of ice crystals divided by the volume of liquid phase remaining between the ice crystals. This ratio will be small during freezing near 0° C. At the same time, vaporization of water from a partially frozen material at temperatures close to ice melting point (for example at −5° C. or above) can be very efficient if performed under vacuum, e.g., below 3 Torr, which is the equilibrium pressure of water vapor above ice at −5° C. At such temperatures, which are considerably higher than $T_g'$, the subject material will be a "slush," a two phase system of ice crystals and a concentrated solution that remains between ice crystals.

Because the chemical potential of water in the slush is equal to the chemical potential of ice, the equilibrium pressure of water vapor above the liquid portion in the slush is equal to that of ice. If the vacuum pressure is below that of the equilibrium pressure, the liquid in the slush overheats and boils. Therefore, subjecting a slush to a vacuum will result in quick vaporization of water from the slush by sublimation from ice crystals, by boiling of the unfrozen solution between ice crystals, and by evaporation from the slush surface simultaneously.

Preservation by Vaporization (PBV) is a preservation process that comprises primary drying and stability drying. Primary drying is performed by intensive vaporization (sublimation, boiling and evaporation) of water at temperatures significantly (approximately 10° C. or more) higher than $T_g'$ from a partially frozen and at the same time overheated (vacuum pressure is below the equilibrium pressure of water vapor) material.

During PBV, the boiling in the course of the primary drying does not produce a lot of splattering because the equilibrium pressure at subzero temperatures above the slush is low and ice crystals on the surface of the slush prevent or inhibit the splattering. Typically, a material (e.g., frozen solutions or suspensions), which has been subjected to PBV drying, looks like a foam partly covered with a skim of a thin freeze-dried cake.

Preventing eruptions (splattering) during the boiling step is important for more effective bulk drying. It is particularly important when Lyoguard tray or other bags covered by water-permeable membranes are used. If splattering takes place, it negatively effects vapor flow through the membrane because the membrane is covered with drops of the material splattered onto its surface. Splattering also negatively affects the appearance of the material after drying in vials. Elimination of splattering also obviates the need for a complex and unreliable "two dimensional" drying protocol discussed above and simplifies the execution of the drying step.

In addition, unlike preservation by foam formation (PFF), preservation by vaporization (PBV) can be very effective for preserving biologicals contained or incorporated within an alginate gel formulation and other gel formulations. A PBV process can be performed by drying frozen gel particles under a vacuum at small negative (on the Celsius scale) temperatures. For such hydrogel systems, vaporization comprises simultaneous sublimation of ice crystals, boiling of water inside unfrozen microinclusions, and evaporation from the gel surface.

PBV is different from freeze-drying because freeze-drying suggests the product processing temperature to be at or below $T_g'$ (which, typically, is below −25° C.) during primary drying and because freeze-drying suggests avoiding the "collapse" phenomenon during both primary and secondary drying. PBV comprises drying at temperatures substantially higher than $T_g'$, i.e., higher than −15° C., better higher than −10° C., and yet better higher than −5° C.

The PFF methods disclosed in U.S. Pat. No. 5,766,520 (Bronshtein) or in WO 96/040077 (Roser and Gibbon)) suggest that freezing of the material to be dried should be avoided during the primary drying.

Stability Drying

Stability drying differs from secondary drying, which is part of a freeze-drying process. Without secondary drying, freeze-dried material will collapse. On the other hand, at the end of primary PBV drying step the material is mechanically stable (i.e., it does not collapse) at room temperature under vacuum. The stability drying is performed (1) to further increase the glass transition temperature of the dry material, (2) to make it mechanically stable at ambient temperatures without vacuum, and (3) to preserve the potency (and, therefore, efficiency) of the biological during a long-term storage at ambient temperatures.

To increase $T_g$ of the material to for example 37° C. and to thereby ensure stabilization at this temperature, the stability drying step should be performed at temperatures significantly higher than 37° C. over many hours to remove water from inside of already dried material.

The process of dehydration of biological specimens at elevated temperatures may be very damaging to the subject biologicals if the temperature used for drying is higher than the applicable protein denaturation temperature. To protect the sample from the damage that can be caused by elevated temperatures, the stability dehydration process (i.e., stability drying) may need to be performed in steps. The first step (either in air or vacuum) should be performed at a starting temperature to ensure dehydration without a significant loss of a biological's viability and potency. After such first drying step, the process of dehydration may be continued in subsequent steps by drying at a gradually higher temperature during each subsequent step. Each step will allow simultaneous increases in the extent of the achievable dehydration and the temperature used for drying during the following step.

For example, in the case of enzyme preservation, it was shown that after drying at a room temperature the drying temperature may be increased to at least 50 degrees Celsius without a loss of enzymatic activity. The extent of dehydration obtained after drying at 50 degrees Celsius will allow a further increase in the drying temperature without a loss of activity, Any given specimen to be preserved is characterized by a maximum temperature it can withstand during the preservation process. However, various protectants and protective co-solutes may provide additional protection to materials during the drying process.

Scaling Up of Bulk Aseptic Drying

PBV process is scalable because evaporative area of the material increases many hundreds of times during formation of a dry mechanically stable specimen. This evaporative area is created because of sublimation of ice crystals and formation of vapor bubbles inside the material. This is true for both drying a hydrogel and for drying a biological solution or suspension.

Drying of a solution or suspension by a PBV process can be performed effectively in 3 to 5 ml vials (0.5 ml fill), 200 ml (10-30 ml fill) vials, small cylindrical Lyoguard® cup containers, and in Lyoguard® trays (250-300 ml fill). At the end of the primary drying by vaporization from the slush state, the material looks like dry foam partially covered with a skim of a freeze-dried cake. At the end of primary drying, the material becomes mechanically stable if stored under a vacuum. High evaporative area of this material allows then to effectively perform a stability drying step under a vacuum by evaporation at elevated temperatures.

Drying of hydrogels is more effective when the hydrogel particles are small (about 1 mm, or below). The reason for that may be that the growth of vapor bubbles nucleated inside gel particles is limited by high viscosity inside the gel. An efficient PBV drying step can be performed when particle size is about or below 0.2 mm. Thus, it has been shown that primary PBV drying of 1.5 kg of an industrial enzyme encapsulated inside alginate gel spherical particles with diameter below 0.2 mm can be done within about six (6) hours. To accomplish that, the gel particles are placed and dried on an open steel tray used in conventional freeze-drying.

The PBV process is beneficial as compared to freeze-drying not only because it is faster, but also because it can be efficiently performed at higher vacuum pressures.

For example at −5° C. or above the PBV primary drying can be effectively performed at several (1 to 3) Torrs in the chamber. Vacuum pressure during freeze-drying should be significantly below 0.476 Torrs, which is the equilibrium pressure above ice at temperatures below −25° Celsius. The process is even more efficient if the pressure is below 0.1 Torr. Because of this, the bags used for balk freeze-drying processing should be characterized by a very high coefficient of permeation for water vapor.

An example of such gas-permeable bag is a product called Lyoguard®, which has been developed by W. L. Gore for bulk lyophilization . . . . The Lyoguard® lyophilization bag is a heat sealable flexible bag. One of its sides is made of plastic that is not permeable to water vapor. Its other side is made of a Gore-Tex® membrane. This membrane is expanded polytetrafluoroethylene (PTFE), nominally containing 0.2 micron pore size, hydrophobic and not permeable to liquid water, but permeable to water vapor.

Because the Lyoguard bag can pass water vapor while still preventing a liquid product from penetrating the membrane and leaking out, it provides a way to process products that require some sterility. A tray could also be applied to animal health products, probiotics, food, etc. Any product for which enclosed container processing may present an advantage can potentially benefit from the use of Lyoguard bags in the preservation by vaporization process. Such advantages may be derived where sterility, ease of handling, isolation of pathogens (e.g., bacteria) from the manufacturing personnel, or enhanced contamination control are desirable.

Lyoguard trays may be used in an industrial-scale PBV processing equipment. However, Lyoguard® trays are characterized by several shortcomings that need to be addressed: (1) the Lyoguard® trays are expensive, and (2) the 0.2 micron pores in expanded polytetrafluoroethylene membranes do not ensure an adequate barrier for viruses, toxins and other dangerous chemicals.

Because PBV (and PFF process) process can be performed at pressures that are considerably higher than those required for freeze-drying, expensive expanded polytetrafluorethylene membranes are not necessary and can be replaced by membranes made of less expensive materials. At the same time, such less expensive membranes can provide for better barriers to prevent viruses, toxins and other dangerous chemicals from leaving the containers used for drying. For example, bags covered with relatively inexpensive Sartorius membranes used for ultrafiltration can be effectively used in industrial-scale PBV drying pursuant to the methods disclosed herein. Other medical grade membranes that can be used to replace expanded polytetrafluoroethylene membranes are 10 to 50 micron polypropylene or polyurethane breathable membranes such as the Medfilm X Medical films manufactured by Mylan Technologies Inc. and various Inspire wound dressing films (e.g., Inspire 1101 (10 μm), 2202 (20 μm), etc.) made by InteliCoat Technologies. It should be understood that many other membranes can be used to implement the disclosed herein methods and apparatus designs.

Using the membranes as described above makes the proposed drying method a barrier aseptic process. A similar approach for using breathable membranes has been disclosed for freeze-drying (see e.g., U.S. Pat. No. 5,309,649).

However, that approach has not been used in the industry because permeation of not porous breathable membranes is too slow for the execution of effective freeze-drying. Therefore performance of PBV or PFF drying in a container (e.g., a bag) covered with a breathable (e.g., polypropylene or polyurethane) membrane without pores presents a novel opportunity for aseptic industrial scale preservation by drying. Because such membranes (which are characterized by a thickness in the range of 20-50 micron) have limited mechanical strength, the design can be reinforced by using a "sandwich" that contains a breathable membrane between two low-cost porous membranes (e.g., Sartorius membranes) that are characterized by a permeability to water vapor and by a higher mechanical strength.

Containers (e.g., bags) for drying pursuant to the inventive methods disclosed herein require suitable connectors that allow to: (1) aseptically introduce a fluid, such as biological solution or/and viral or cellular suspension, into a container without collapsing the container, (2) aseptically dry the fluid, (3) aseptically store the dry specimen in the container, and (4) transfer the finished dry product from the container to other devices for downstream processing (e.g., milling, mixing, packaging, transportation, etc.). Preferably, the containers used in the disclosed novel methods should be less expensive than the costly Lyoguard trays covered with expensive membranes.

Equipment for Continuous Load Industrial Production.

Now, an embodiment of equipment for industrial-scale implementation of the novel methods for preservation of biologicals will be described. It should be understood that the described embodiments are presented herein only for illustration purposes. A person skilled in the art of preservation of biologicals will be able to easily use the same ideas to design other equipment and processes which should be considered within the spirit and scope of the invention disclosed herein.

There are several barriers that water vapor has to go through on the way from the specimen to be dried to the condenser. First, the vapor passes the membrane that covers the specimen container (e.g., a bag or tray used for bulk drying) or leaves the vials through holes under the stoppers during the unit doze drying. Second, the vapor must travel from the drying chamber to condenser.

Because freeze-drying is performed at very low pressures, the vapor flow between the drying chambers and the condenser "chokes," thereby limiting the speed of the drying process. For this reason, a typical industrial freeze-dryer that can condense many liters of water from the subject material in a given time is currently built as a one-chamber apparatus in which the diameter of the connector between the chamber and the condenser must be relatively large (typically, about 1 meter or more). This is the reason why industrial scale vacuum freeze-dryers cannot be built utilizing a manifold design, i.e. an apparatus with a number of large chambers.

Unlike the equipment that uses a freeze-drying process, equipment that uses a PBV process makes it possible to build manifold-based PBV or manifold-based PFF equipment because the primary drying for those processes can be performed at considerably higher vacuum pressures (for example 1 to 3 Torrs), thereby allowing for considerably higher flows between the chambers and the condenser. For example it has been established in practice that primary PBV drying of 4.5 Kg of an industrial enzyme incorporated inside alginate beads inside a vacuum chamber of modified Genesis freeze-dryer (from Virtis Co) can be accomplished within about six hours. The apparatus used in that process has a connector between the drying chamber and the condenser with a diameter of only about 0.1 meter. Likewise, it has been reported (U.S. Pat. Nos. 6,306,345 and 6,692,695) that an apparatus that utilizes a PFF process is capable of removing a similar amount of water from a chamber to a condenser through a connector with a similar diameter within several hours. Therefore, equipment that utilizes either a PBV or PFF process can be built using a manifold drying apparatus design, thereby providing for a continues load (and, thus, faster and more efficient) production.

A manifold dryer can be designed and built as a large condenser, which communicates through a plurality of connectors with a plurality of drying chambers. The connectors may optionally be can equipped with vacuum valves (or other suitable devices) to control or close the flow of air or water vapors from the chamber into the condenser. The material to be dried is placed in the chambers. A single or a plurality of heat sources are provided for conveying heat to the chambers in order to compensate for a loss of energy due to evaporation during the drying process. Additionally, a cooling device is provided to allow cooling of the material before the drying step to about −10° C. The cooling device may utilize any known conventional design for refrigeration equipment, i.e. it may comprise a compressor and a heat exchanger.

The chambers can, for example, be cylindrical as disclosed in U.S. Pat. No. 6,692,695. The chambers also may be flat to accommodate a tray filled with vials, or bags like Lyoguard bag.

The heat can be delivered by conduction, infrared radiation, using low frequency 50 Hz-500 Hz), radio frequency (5 MHz-60 MHz) electromagnetic heating of the material in the slush state during primary drying, or by any other known source or method of heat generation and transfer.

The apparatus may also be equipped with an optional control system that will control the various processes. For example, the control system can provide automatic or other control of the heating, gas flows, cooling, and other functions of the apparatus. Additionally, the control system could be programmable. It also may be programmed to advantageously schedule the progress of the drying processes in various chambers of the apparatus. This feature will allow to connect a new chamber to the manifold and disconnect a chamber where the drying process is finished from the dryer within predetermined periods of time, e.g., every hour, or 30 minutes. Thus, if the chamber capacity is 5 Kg and a new chamber is attached every 30 minutes, the production throughput of one chamber will equate to about 240 kg per day, i.e., 10 Kg per hour. It will be appreciated by those skilled in the art that such throughputs are considerably higher than those achievable by conventional freeze-drying equipment.

The manifold-type equipment design described above can provide a production rate that is limited only by the capacity of the condenser. If instead of using a mechanical refrigeration device, liquid nitrogen is used to cool the condenser, considerably higher production rates can be achieved. Even more importantly from the industrial production standpoint, manifold drying equipment that utilizes either a PFF or a PBV process allows to perform continuous load high-speed manufacturing that, as discussed above, is impossible using a freeze-drying process.

It shall be understood that there is a large plurality of ways to design and build the novel equipment disclosed herein that will be consistent with novel principles of the invention hereof. For example, the mechanical design of the drying chambers, the design and configuration of the connectors, the geometry of the manifold, etc. can take many different forms. All such various design and engineering solutions shall be understood to be within the spirit and scope of the invention disclosed herein.

Quality of Preservation.

A number of feasibility experiments have been conducted which demonstrate the methods disclosed herein are functional and effective. For example, a live viral enveloped vaccine has been stabilized with no loss of activity after drying pursuant to a PBV method and subsequent storage at 40. degree. C. for one month. In addition, enzymes and ice nucleating proteins have been preserved using the PBV method with no loss of activity. After a preservation by vaporization, the material can be milled or otherwise processed to make it suitable for specific modes of delivery.

EXAMPLES

The following examples are offered only to illustrate, but not to limit the claimed invention.

Example 1

Preservation of Ice Nucleating Bacteria Using a PFF Process

To obtain ice nucleating bacteria (INB), a preservation mixture of 180 g of concentrated suspension of ice nucleating bacteria *Pseudomonas* Syringae ATCC 53543 were mixed with 108 g of sucrose and 12 g of maltrin. The mixture was then mixed until sugars were completely dissolved.

The resulting mixture was placed in 100 ml serum vials. Thus, 16.66 g of the mixture was placed inside each vial. The mixture in the vials then was dried inside an "Ultra" freeze-drying machine made by Virtis Corporation and modified for better vacuum pressure control in the drying chamber. The vials were placed on the surface of a stainless steel shelf inside the drying chamber. The shelf temperature was maintained by circulating ethylene glycol/water antifreeze at a controlled temperature inside the shelf. Specimens were preserved using a preservation by foam formation process described in U.S. Pat. No. 5,766,520. No freezing was observed in the vials during the preservation. After stable dry foams formed inside the vials, the foams were dried at 50° C. for 24 hours under high vacuum. After that, the vials were closed with rubber stoppers under vacuum and sealed with aluminum seals. A lot of splattering was observed on the walls of the vials. The intensive splattering took place during the boiling of the material inside the vials. All glass walls of the vials were covered with small (1 mm or less in diameter) drops of the mixture.

The dry material in vials was irradiated to sterilize the material. Sterility was tested by plating of reconstituted bacteria on different agar media. No bacterial growth was observed. Ice nucleating activity of preserved INB was measured after the sample reconstitution with 100 ml of 0.01M phosphate buffer. Ice nucleating activity was measured as a concentration of ice nucleating centers that can nucleate an ice crystal in a 10 μl buffer drop during 5 minutes at −5 degrees Celsius. The results of the assay show that more than 50% of ice nucleating activity remained in the preserved samples even after the radiation treatment. No decrease in the activity of the INB was observed during the subsequent storage at room temperature and 37° C.

Example 2

Preservation of Ice Nucleating Bacteria Using a PBV Process

Five vials with preserved INB bacteria from Example 1 above were reconstituted with 9 g of water. The vials were placed in the "Ultra" freeze-drying machine (made by Virtis Corporation). Before application of vacuum, the shelf was precooled to −10° C. and the material inside the vials froze. Than vacuum was applied simultaneously with increasing the shelf temperature to 35° C. The vacuum pressure was controlled so that the temperature inside the vials was maintained between −5° C. and −10° C. After about 3 hours, the primary drying was complete with no visible splattering of the material on the walls of the vials. The dry material looked like foam in partly covered with a skim of thin freeze-dried cake. After a stable dry material formed inside the vials, the material was dried at 50° C. for 24 hours under a high vacuum. After that, the vials were closed with rubber stoppers and sealed with aluminum seals. The results of the assay performed after reconstituting the vials with 100 ml of 0.01M phosphate buffer show no statistically significant decrease of activity after the PBV drying.

Preservation of Isocitrate Dehydrogenase Solution by a PBV Process

An aqueous 50% glycerol isocitrate dehydrogenase solution from Sigma Chemical Co. was dialyzed for 5 hours in 0.1 M TRIS HCl buffer (pH 7.4). The activity of the isocitrate dehydrogenase (IDH) in the 0.1 M TRIS HCl solution after dialysis was 23±1 units per ml. The dialyzed IDH was mixed 1:1 with preservation solution containing 30% sucrose and 15% raffinose, filled in 5 ml vials (0.5 ml per vial) and placed on the shelf of "Genesis" (made by VirTis Corporation) freeze-dryer modified to provide better vacuum pressure control in the drying chamber. The material was first frozen by cooling the shelf to −15° C. Then a vacuum (1 Torr) was applied simultaneously with raising the shelf temperature to 45° C.

After about 1 hour the vacuum was increased (the pressure was decreased below 0.2 Torrs). Then the material was dried overnight and sealed with rubber stoppers; vacuum was released and the vials were places at 37° C. After drying, the material looked like a foam partly covered with a skim of freeze-dried cake. No splattering was observed on the walls of the vials. After one month of storage at 37° C., the specimens were reconstituted with 0.375 ml of water and activity of IDH was measured. The reconstituted samples were tested for activity by assaying ability to reduce NADP, measured spectrophotometrically at 340 nm. The reaction mix included: 2 ml 0.1 M TRIS HCl buffer, pH 7.4; 10.mu.l of 0.5% by weight NADP+; 10 μl of 10 Mm $MnSO_4$; 10 μl of 50 Mm 1-isocitrate; and 10 μl of reconstituted IDH solution. The activity was 11±0.5 units/ml, which means there was no significant loss of activity during drying and during the month of subsequent storage at 37° C.

Example 4

PBV Preservation of *Lactobacillus Acidophilus* ATCC 4356

*Lactobacillus acidophilus* ATCC 4356 is the type strain of this commercially significant species. *L. acidophilus* (probiotics) grows by fermentation of lactose, glucose and a range of carbohydrates. The end product of this fermentation is almost Solutions Used:
1. Difco MRS broth containing 0.05% cysteine and 0.1% of Ca Cl2;
2. MRS agar;
3. 10% cysteine, Dubecco's phosphate buffered saline (DPBS);
4. Preservation Solution-1 (PS-1): 20% sucrose, 10% MSG; 0.1% of reconstituted INB from Experiment 1.
5. Preservation Solution-2 (PS-2): 20% sucrose, 10% MSG, 1% alginate; 0.1% of reconstituted INB from Experiment 1.
6. EDTA-1 solution for reconstitution of dry gel powder comprising 45 g of 0.2M KH2PO4+30 g of 0.3M K2HPO4+75 g of water+15 g of standard EDTA solution from J. T. Baker.

Preculture Growth:
Steps:
1. L. acidophilus, strain 4356, obtained from ATCC was used to inoculate 150 ml of MRS broth+0.05% cysteine.
2. The preculture were grown in Belco spin flask at 37° C. incubator with gently stirring overnight. At the end the optical density A (600) in preculture was 3.027 and pH was 4.03.

Fermentation:
Fermentation was performed using a New Brunswick Scientific Company BioFlo 2000 fermentor with a 2 L working capacity.
Steps:
1. 2 L of MRS broth was prepared from commercial Difco powder and autoclaved inside BioFlo 2000 fermentor for 30 min. (liq. cycle)
2. 10 ml of 10% cysteine were added into fermentor to obtain final concentration of cysteine=0.05%
3. 20 ml of preculture were inoculated into the fermentor.
4. Fermentor was operated at 37 C, 50 RPM agitation, with no pH regulation.
5. Optical density A (600) and pH after 9 hrs of fermentation remained stable. A (600)=2.9-3.0; pH=4.08-4.00.
6. After 10.5 hrs of fermentation the fermentor was harvested and culture distributed into 8.times.250 ml centrifuge tubes, 250 g of culture into each tube.
7. The tubes were centrifuged at 4 C, 3000 rpm, for 15 min.
8. Supernatant was decanted off.

Preparation of Specimens for Drying
Steps:
1. To prepare preservation mixture-1 (PM-1) the pellets in 7 tubes were reconstituted with PS-1 (50 g of PS-1 into each tube). The mixtures were thoroughly vortexes and merged together.
2. To prepare the preservation mixture-2 (PM-2) the pellet in remaining 8th tube was reconstituted with 50 g of PS-2. The mixture was thoroughly vortexes
3. PM-1 was distributed into 50.times.5 ml serum vials, 0.5 g per vial (Formulation 1).
4. PM-1 was filled into each of 5 small cylindrical Lyoguard containers (caps), 10 g per a cap (Formulation 2).
5. 250 g of PM-1 was placed in a Lyoguard tray (Formulation 3).
6. 10 g of PM-2 released through the 20G needle in a bath containing 2% CaCl2 dissolved in 90% PS-1 to form gel particles looking like spaghetti. The gel particles were collected using 90 micron sieve. The liquid outside gel particles was sacked out using laboratory vacuum pump. The particles were placed in a small cylindrical 200 ml Lyoguard containers (caps). 5 caps were filled (Formulation 4).
7. Activity of bacteria in PM-1 and PM-2 before drying was determined by plating of 0.1 ml of a PM diluted millions times on MRS agar+0.05% cysteine.
8. All plates were stored under anaerobic condition at 37° C. incubator for 48 hrs.

Drying Protocol.
1. Initial shelf temperature was set to 0° C.;
2. Specimens froze after the temperature inside the specimens decreased to approximately −4° C. as a result evaporation after vacuum application. The freezing began at the surface of the specimens. After that the shelf temperature was increased to 35° C.
3. The primary drying was performed by keeping the temperature inside the specimens between −5° C. and −10° C. to obtain mechanically stable dehydrated state. After drying the material in the vials and in Lyoguard tray looked foamy with a skim of freeze-dried cake above the foam. The alginate particles looked like dry spaghetti.
4. The stability drying was performed under complete vacuum first at 25° C. overnight. Then shelf temperature was raised to 50° C. for additional 48 hrs.
5. After drying in glass vials the mass of dry material in a vial was approximately 0.15 g
6. After drying, materials from caps and tray were milled in dry room (at 15% relative humidity) using VirTis laboratory homogenizer. The milled powders were filled in 5 ml glass vials (0.15 g per vial). The vials were sealed with robber stoppers covered with aluminum seals.
7. To measure the activity of 0.15 g of dry material in each vial was reconstituted with 4.85 ml of DPBS and than diluted an additional 100,000 times before 0.1 ml was plated on MRS agar+0.05% cysteine.
8. To measure the activity of 0.15 g of dry material containing alginate was reconstituted with 4.85 ml of EDTA-1 solution and than diluted an additional 100,000 times before 0.1 ml was plated on MRS agar+0.05% cysteine.

Results are shown in Table 2 below:

TABLE 2

| Storage conditions | Number of colonies | | | |
|---|---|---|---|---|
| | Form. PM-1 | Fo PM | Form PM-1 | For PM-2 |
| Right before drying | 168 ± 1 | M 76 | 173 ± | 2 |
| Right after | 79 ± 8 | 76 | 66 ± 6 | 72 ± |
| 1 week at RT | 75 ± 9 | 70 | 72 ± 1 | 79 ± |
| 1week at | 83 ± 1 | 69 | 69 ± 12 | 148 ± |
| 1 month at | 82 ± 1 | 86 | 84 ± 7 | 63 ± |
| 1 month at | 77 ± 1 | 71 | 57 ± 7 | 54 ± |

It shall be understood that the examples and embodiments described herein are for illustrative purposes only and that various modifications or changes in light thereof that may be suggested to persons skilled in the art are within the spirit and are to be included within the purview of this disclosure and scope of the claims that follow.

While the foregoing invention has been described in some detail for purposes of clarity and understanding, it will be clear to one skilled in the art from a reading of this disclosure that various changes in the form and detail can be made without departing from the true scope of this invention. For example, the formulations, techniques, apparatus and specific process parameters described herein can be used in various combinations and/or adjusted to suit a specific biological without departing from the scope of the disclosed and claimed inventions. All publications, patents, patent applications, and/or other documents cited in this application are incorporated by reference in their entirety for all purposes to the same extent as if each individual publication, patent, patent application and/or other document were individually indicated to be incorporated by reference for all purposes.

U.S. PATENT DOCUMENTS

U.S. Pat. No. 4,215,153 July, 1980 Kai et al.
U.S. Pat. No. 4,396,563 August, 1983 Gusmer.
U.S. Pat. No. 4,451,569 May, 1984 Kobayashi et al.
U.S. Pat. No. 4,559,298 December, 1985 Fahy.
U.S. Pat. No. 4,642,903 February, 1987 Davies et al.
U.S. Pat. No. 4,891,319 January, 1990 Roser.
U.S. Pat. No. 5,026,566 June, 1991 Roser.
U.S. Pat. No. 5,030,469 July, 1991 Mergelsberg.
U.S. Pat. No. 5,039,540 August, 1991 Ecanow et al.
U.S. Pat. No. 5,079,018 January, 1992 Ecanow et al.
U.S. Pat. No. 5,084,101 January, 1992 Engles et al.
U.S. Pat. No. 5,149,653 September, 1992 Roser.
U.S. Pat. No. 5,190,987 March, 1993 Parkinson.
U.S. Pat. No. 5,200,399 April, 1993 Wettlaufer et al.
U.S. Pat. No. 5,250,429 October, 1993 Jolly et al.
U.S. Pat. No. 5,252,620 October, 1993 Elliott et al.
U.S. Pat. No. 5,290,582 March, 1994 Dressel et al.
U.S. Pat. No. 5,354,558 October, 1994 Britton et al.
U.S. Pat. No. 5,425,951 June, 1995 Goodrich, Jr., et al.
U.S. Pat. No. 5,439,945 August, 1995 Smies.
U.S. Pat. No. 5,565,318 October, 1996 Walker et al.
U.S. Pat. No. 5,597,416 January, 1997 Fuisz et al.
U.S. Pat. No. 5,621,094 April, 1997 Roser.
U.S. Pat. No. 5,648,206 July, 1997 Goodrich, Jr. et al.
U.S. Pat. No. 5,762,961 June, 1998 Roser et al.
U.S. Pat. No. 5,766,520 June, 1998 Bronshtein.

FOREIGN PATENT DOCUMENTS

RU 959786 September, 1982
WO 9314191 July, 1993
WO 9640077 December, 1996
1. Annear, "Preservation of Leptospir.ae butted. by drying" J. Path. Bact. vol., 72, pp. 322-323, 1956:
2. Annear, "Observations of the Preservation by Drying of Leotospirae and Some Other Bacteria", Austral J. Exp. Biol. vol., 36, pp. 1-4: 1958.
3. Annear, "Observation on Drying Bacteria from the Frozen and From the Liquid State" Austral. J. Exp Biol. vol. 36, pp. 211-221, 1958.
4. Annear, "Recovery of Strigomonas oncopeltii after Drying From the Liquid State" Aust. J. Exp. Biol., vol. 39, pp. 295-303, 1961.
5. Annear, "Preservation of the Reiter Treponeme by Drying From the Liquid State", J. Bact., vol. 83, pp. 932-933, 1962.
6. Annear, "The Preservation of Leptospires by Drying From the Liquid State", J. Gen. Microbiol., vol. 27, pp. 341-343, 1962.
7. Annear, "Recoveries of Bacteria After Drying on Cellulose Fibres A Method for The Routine Preservation of Bacteria", Austral. J. Exp. Biol., vol. 40, pp. 1-8, 1962.
8. Annear, "Preservation of Yeast by Drying", Austral. J. Exp. Biol., vol. 41, pp. 575-580, 1963.
9. Annear, "Recoveries of Bacteria After Drying In Glutamate and Other Substances", Aust. J. exp. Biol. Med. Sci., vol. 42, pp. 717-722, 1964.
10. Annear, Recoveries of Bacteria After Drying in Vacuo at a Bath Temperature of 100° C., Nature, No. 5050, p. 761, Aug. 13, 1966.
11. Annear, Survival of Bacteria in Desiccates at 100° C. in Dry Atmospheres, Nature vol. 206 No. 4991, pp. 1373-1374, Jun. 26, 1965.
12. Bronshtein, V. 1998. Preservation by foam formation. U.S. Pat. No. 5,766,520.
13. Burke, M. J. 1986. The glassy state and survival of anhydrous biological systems. In "Membranes, Metabolism, and Dry Organisms", p. 358-363, Ed. C. Leopold, Cornell University Press, Ithaca, N.Y.
14. Annear, D. I. (1958) Observations on drying bacteria from the frozen and from the liquid state. Austral. J. Exp. Biol., 36: 2111-222.
15. Bronshtein, V. 2004. Preservation by Foam Formulation, an Alternative to Freeze-Drying. Pharmaceutical Technology. 28: 88-91.
16. Bronshtein V. (2003) Scalable long-term shelf preservation of sensitive biological solutions and suspensions. U.S. Pat. No. 6,509,146.
17. Bronshtein, V. (2002) "Good" and "Bad" glasses for long-term preservation of biologicals. In: "Cryo 2002 programn", Abstract S88 of a Paper Presented at the 39th Annual Meeting of the Society for Cryobiology, Breckenridge, Colo.
18. Bronshtein, V. (2002) Preservation of viruses and bacteria at ambient temperatures with methylglucoside. In: "Cryo 2002 program", Abstract S55 of a Paper Presented at the 39th Annual Meeting of the Society for Cryobiology, Breckenridge, Colo.
19. Bronshtein, V. (2001) Preservation and Formulation of Bioactive Materials for Storage And Delivery in Hydrophobic Carriers. WO00137656.
20. Bronshtein, V. (1998) Preservation by foam formation. U.S. Pat. No. 5,766,520. [0202]
21. Bronshtein V., Braken R. B., Campbell, J. G. (2003) Bulk Drying and the Effect of Inducing Bubble Nucleation. US2003/0155669.
22. Bronshtein, V., Bracken, Kevin R., Livers, Ronnie K., and Williams, D. R. (2001) Industrial Scale Barrier Technology For Preservation Of Sensitive Biological Materials at Ambient Temperatures. U.S. Pat. No. 6,306,345.
23. Bronshtein, V., Frank, J. L., and Leopold, A. C. (1996). Protection of desiccated enzymes by sugars. In: "Cryo 96 program", Abstract 22 of a Paper Presented at the 33rd Annual Meeting of the Society for Cryobiology, Indianapolis, Ind.
24. Bronshtein, V., Isaac, Ch., and Djordjevic G. (2001) Preservation of Bacterial Cells at Ambient Temperatures. WO00112779.
25. Bronshtein, V., Isaac, C. (1999) Stabilization of bacterial cultures by VitriLife$^{SM}$ preservation process. In: "Proceedings of the 17th International Conference of the International Committee on Food Microbiology and Hygiene (ICFMH)", Veldhoven, The Netherlands, pp. 221-225.
26. Bronshtein, V., and Leopold, A. C. (1996) Accelerated aging of dried luciferase and isocitrate dehydrogenase. Effect of sugar/enzyme mass ratio. In: "Cryo 96 program", Abstract 23 of a Paper Presented at the 33rd Annual Meeting of the Society for Cryobiology, Indianapolis, Ind.
27. Bronshtein V., Lynkowsky L. (2001) Formulation of preservation mixtures containing sensitive biologicals to be stabilized for ambient temperature storage by drying. WO00137656. 29. Bronshteyn, V. L. and Chemov A. A.

(1991) Freezing potentials arising on solidification of dilute aqueous solution of electrolytes. J. Crystal Growth 112: 129-145.
30. Bronshtein, V. L. 1989. The theory of crystallization hydrolysis. Cryobiology 26:582-583 (Abstract 137, 26th Annual Meeting, Society for Cryobiology).
31. Bronshtein, V. L., Y. A. Itkin, G. G. Shurda, and P. G. Iserovich. 1983. Mechanism of lactic acid *Streptococcus cremoris* T1815 damage during freezing. Kriobiologia i Kriomeditsina 12: 31-35.
32. Burke M. J. (1986) The glassy state and survival of anhydrous biological systems. In "Membranes, Metabolism, and Dry Organisms", 358-363, Ed. C. Leopold, Cornell University 33. Bruni, F. and Leopold A. C., 1992. Pools of water in anhydrobiotic organisms: a thermally stimulated depolarization current study Biophys. J. 63, 663.
34. Dye, C., S. Scheele, P. Dolin, V. Pathania, and M. C. Raviglione. 1999. Consensus statement. Global burden of tuberculosis: estimated incidence, prevalence, and mortality by country. WHO Global Surveillance and Monitoring Project. JAMA. 282:677-686.
35. Frieden, T. R., T. R. Sterling, S. S. Munsiff, C. J. Watt, and C. Dye. 2003. Tuberculosis. The Lancet 362:887-899.
36. Franks, F. 1990. Freeze drying: From empiricism to predictability. Cryo-Letters 11, 93-100.
37. Johari, G. P., Astl, G., and Mayer, E. (1990) Enthalpy relaxation of glassy water. J. Chem. Phys., 809-810,
38. Jennings T. A. (2002) Lyophilization. Interpharm/CRC Press LLC. 646 ps.
39. Roser, B. J. and E. M. Gribbon. 1996. Methods for stably incorporating substances within dry, foamed glass matrices and compositions obtained thereby. Patent WO9640077
U.S. Pat. No. 4,609,102 1986-09 Blum Plastic film bag lyophilization system
U.S. Pat. No. 4,973,327 1990-11 Goodrich et al. Cryopharm Blood bag for lyophilization
U.S. Pat. No. 5,257,983 1993-11 Garyantes et al. Cryopharm Corporation Blood bag for lyophilization
U.S. Pat. No. 5,309,649 1994-05 Bergmannn et al. Boelringer Mannheim Gmbh Process and container for freeze drying under sterile conditions
USD425205 2000-05 Henigan et al. Gore Enterprise Holdings, Inc. Lyophilization container
USD430939 2000-09 Zukor et al. Gore Enterprise Holdings, Inc. Lyophilization container
U.S. Pat. No. 6,517,526 2003-02 Tamari Container for lyophilizing biological products 40.

The invention claimed is:

1. A method for preserving one or more therapeutically active biologicals, comprising:
partially freezing a suspension comprising:
one or more therapeutically active biologicals;
one or more protective excipients; and
an aqueous solution
by cooling to a temperature above −20° C. to obtain a slush comprising a mixture of ice crystals and a liquid between the ice crystals;
performing primary drying of the slush under conditions to prevent or inhibit splattering of the liquid to provide a mechanically stable foam optionally comprising a skim of a thin freeze-dried cake;
wherein the conditions comprise applying temperatures above −20° C. and a vacuum pressure below 3 Torr so the liquid boils and the ice crystals sublime; and
performing secondary drying by desorbing water from the mechanically stable foam under high vacuum at ambient temperature or above to increase the foam's glass transition temperature to provide preserved therapeutically active biologicals in a glassy matrix that is stable at ambient temperatures; and
wherein the biologicals are not subjected to temperatures equal to $T_g'$ or below, wherein $T_g'$ is the temperature at which the suspension completely solidifies during cooling.

2. The method according to claim 1, wherein the one or more therapeutically active biologicals comprises blood, blood components, animal cells loaded with nonreducing disaccharides, nonreducing derivatives of monosaccharides, arbutin, or amino acids.

3. The method of claim 1, wherein the one or more therapeutically active biologicals is selected from the group consisting of peptides, proteins, nucleic acids, antibodies, vaccines, bacteria, viruses, liposomes, platelets and other blood components, and mammalian cell suspensions.

4. The method of claim 1, wherein at least one of the one or more therapeutically active biologicals is an attenuated viral vaccine comprising live viruses selected from the group consisting of influenza virus, parainfluenza virus, AAV, adenovirus, respiratory syncytial virus, herpes simplex virus, cytomegalovirus, SARS virus, corona virus family members, human metapneumovirus, and Epstein-Barr virus, measles, mumps, and rubella.

5. The method according to claim 1, wherein the one or more protective excipients comprises a nonreducing monosaccharide, sugar alcohol, oligosaccharide, amino acid, polyvinylpyrrolodone, polyethylene glycol, Ficol, Inulin, albumin, gelatin, whey proteins, and/or a polaxomer.

6. The method of claim 1, wherein the one or more therapeutically active biologicals in a glassy matrix has a moisture content from about 0.01% to about 2%.

7. The method of claim 1, wherein the conditions of primary drying comprise a temperature of at least 10° C. higher than $T_g'$.

8. The method of claim 1, wherein the conditions of primary drying comprise a temperature of −15° C. or higher.

9. The method of claim 1, wherein the conditions of primary drying comprise a temperature of −10° C. or higher.

10. The method of claim 1, wherein the conditions of primary drying comprise a temperature of −5° C. or higher.

11. The method of claim 1, wherein performing secondary drying further comprises applying a temperature of 37° C. or higher.

12. The method of claim 1, wherein the one or more therapeutically active biologicals are mechanically stable at ambient temperature without vacuum.

13. The method of claim 1, further comprising reconstituting the one or more therapeutically active biologicals in water, wherein the one or more therapeutically active biologicals do not lose biological activity.

14. The method of claim 1, wherein providing the biological suspension further comprises encapsulating the one or more therapeutically active biologicals as a hydrogel.

15. A scalable method for preserving one or more therapeutically active biologicals, comprising:
partially freezing a suspension comprising:
one or more therapeutically active biologicals;
one or more protective excipients; and
an aqueous solution
by cooling to a temperature higher than −20° C. to obtain a slush comprising a mixture of ice crystals and liquid between the crystals;

performing primary drying of the slush under conditions to prevent or inhibit splattering of the liquid to provide a mechanically stable foam;

wherein the conditions comprise applying a temperature above −20° C. and a vacuum pressure below 3 Torr so the liquid boils and the ice crystals sublime; and performing secondary drying of the mechanically stable foam under high vacuum at ambient temperature; and continuing the secondary drying at temperatures greater than 40° C. to provide preserved therapeutically active biologicals in a glassy matrix that is stable at ambient temperatures for long term storage; and wherein the biologicals are not subjected to temperatures equal to $T_g'$ or below, wherein $T_g'$ is the temperature at which the suspension completely solidifies during cooling.

16. The method according to claim 15, wherein the one or more therapeutically active biologicals comprises blood, blood components, animal cells loaded with nonreducing disaccharides, nonreducing derivatives of monosaccharides, arbutin, or amino acids.

17. The method of claim 15, wherein the one or more therapeutically active biologicals is selected from the group consisting of peptides, proteins, nucleic acids, antibodies, vaccines, bacteria, viruses, liposomes, platelets and other blood components, and mammalian cell suspensions.

18. The method of claim 15, wherein at least one of the one or more therapeutically active biologicals is an attenuated viral vaccine comprising live viruses selected from the group consisting of influenza virus, parainfluenza virus, AAV, adenovirus, respiratory syncytial virus, herpes simplex virus, cytomegalovirus, SARS virus, corona virus family members, human metapneumovirus, and Epstein-Barr virus, measles, mumps, and rubella.

19. The method according to claim 15, wherein the one or more protective excipients comprises a nonreducing monosaccharide, sugar alcohol, oligosaccharide, amino acid, polyvinylpyrrolodone, polyethylene glycol, Ficol, Inulin, albumin, gelatin, whey proteins, or a polaxomer.

20. The method of claim 15, wherein the one or more therapeutically active biologicals has a moisture content from about 0.01% to about 2%.

21. The method of claim 15, wherein primary drying comprises applying a vacuum pressure of about 1 to 3 Torr.

22. The method of claim 15, wherein primary drying comprises a temperature of at least 10° C. higher than $T_g'$.

23. The method of claim 15, wherein primary drying comprises a temperature of −15° C. or higher.

24. The method of claim 15, wherein primary drying comprises a temperature of −10° C. or higher.

25. The method of claim 15, wherein primary drying comprises a temperature of −5° C. or higher.

* * * * *